(12) United States Patent
Zar et al.

(10) Patent No.: US 11,844,619 B2
(45) Date of Patent: *Dec. 19, 2023

(54) VOLUMETRIC LAT MAP

(71) Applicant: Biosense Webster (Israel) Ltd., Yokneam (IL)

(72) Inventors: Lior Zar, Poria Illit (IL); Benjamin Cohen, Haifa (IL); Natan Sharon Katz, Atlit (IL); Aharon Turgeman, Zichron Ya'acov (IL); Yaron Kadoshi, Hosha'aya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,470

(22) Filed: Jan. 9, 2023

(65) Prior Publication Data
US 2023/0157612 A1    May 25, 2023

Related U.S. Application Data

(63) Continuation of application No. 16/817,537, filed on Mar. 12, 2020, now Pat. No. 11,564,610.

(60) Provisional application No. 62/852,266, filed on May 23, 2019.

(51) Int. Cl.
| | |
|---|---|
| *G06T 7/00* | (2017.01) |
| *G06T 17/00* | (2006.01) |
| *A61B 5/316* | (2021.01) |
| *G16H 50/50* | (2018.01) |
| *A61B 5/339* | (2021.01) |
| *G06T 7/33* | (2017.01) |

(Continued)

(52) U.S. Cl.
CPC .............. *A61B 5/316* (2021.01); *A61B 5/339* (2021.01); *G06T 7/0012* (2013.01); *G06T 7/344* (2017.01); *G06T 17/00* (2013.01); *G16H 50/50* (2018.01); *A61B 5/283* (2021.01); *A61B 5/4836* (2013.01); *G06T 2207/30048* (2013.01)

(58) Field of Classification Search
CPC ......... A61B 5/316; A61B 5/339; A61B 5/283; A61B 5/4836; A61B 5/287; A61B 34/10; A61B 2034/105; A61B 2034/108; G06T 7/0012; G06T 7/344; G06T 17/00; G06T 2207/30048; G16H 50/50
See application file for complete search history.

(56) References Cited

U.S. PATENT DOCUMENTS

| | | | | |
|---|---|---|---|---|
| 5,687,737 A | * | 11/1997 | Branham | A61B 5/287 600/509 |
| 2006/0084970 A1 | | 4/2006 | Beatty et al. | |
| 2013/0057548 A1 | | 3/2013 | Schreckenberg | |

(Continued)

*Primary Examiner* — Siamak Harandi
(74) *Attorney, Agent, or Firm* — Frost Brown Todd LLP

(57) ABSTRACT

A method includes assigning, to first voxels in a model of tissue of a chamber of a heart, respective first values of a parameter at respective locations on the tissue, the first voxels representing the locations, respectively. Some of the locations are on an endocardial surface of the tissue, and others of the locations are on an epicardial surface of the tissue. The method further includes assigning respective second values to second voxels in the model, a subset of which represent a portion of the tissue between the endocardial surface and the epicardial surface, by interpolating the first values. Other embodiments are also described.

20 Claims, 3 Drawing Sheets

(51) Int. Cl.
*A61B 5/00* (2006.01)
*A61B 5/283* (2021.01)

(56) References Cited

U.S. PATENT DOCUMENTS

2017/0221254 A1  8/2017  Zar et al.
2017/0281031 A1  10/2017  Houben et al.
2020/0367778 A1  11/2020  Zar et al.

* cited by examiner

VOLUMETRIC LAT MAP

CROSS-REFERENCE TO RELATED APPLICATION

The present application is a continuation of U.S. Non-Provisional application Ser. No. 16/817,537, entitled "Volumetric Lat Map," filed Mar. 12, 2020, issued as U.S. Pat. No. 11,564,610 on Jan. 31, 2023, which claims the benefit of U.S. Provisional Appl. No. 62/852,266, entitled "Volumetric LAT map," filed May 23, 2019, the disclosure of which are incorporated herein by reference in their entirety.

FIELD OF THE INVENTION

The present invention is related to anatomical and electrophysiological models, particularly of the heart.

BACKGROUND

A local activation time (LAT) at a particular location on the tissue of a heart is the time at which the wavefront of electrical propagation passes through the location. A local activation time is typically measured from a particular reference time, such as a point in time in the QRS complex of a body-surface electrocardiogram (ECG) recording.

US Patent Application Publication 2006/0084970, now abandoned, describes a method of acquiring and mapping physiological data in a heart chamber. The method includes inserting a catheter having an electrode into the heart chamber. Physiological data in the heart chamber is acquired with the electrode. The position of the electrode is determined, and the location of the acquired physiological data is determined using the position of the electrode. The acquired physiological data is integrated with the location of the acquired physiological data. Information related to the three-dimensional geometry of at least a portion of the heart chamber is received, and a continuous three-dimensional color-coded map of the physiological data is created and superimposed on a geometrical representation of the three-dimensional geometry information. The map is then utilized to deliver ablation therapy.

US Patent Application Publication 2016/0100770, issued as U.S. Pat. No. 9,675,266 on Jun. 13, 2017, describes a system for diagnosing arrhythmias and directing catheter therapies, which may allow for measuring, classifying, analyzing, and mapping spatial electrophysiological (EP) patterns within a body. The system may further guide arrhythmia therapy and update maps as treatment is delivered. The system may use a medical device having a high density of sensors with a known spatial configuration for collecting EP data and positioning data. Further, the system may also use an electronic control system (ECU) for computing and providing the user with a variety of metrics, derivative metrics, high definition (HD) maps, HD composite maps, and general visual aids for association with a geometrical anatomical model shown on a display device.

SUMMARY OF THE INVENTION

There is provided, in accordance with some embodiments of the present invention, a system including a monitor and a processor. The processor is configured to assign, to first voxels in a model of tissue of a chamber of a heart, respective first values of a parameter at respective locations on the tissue, the first voxels representing the locations, respectively. Some of the locations are on an endocardial surface of the tissue, and others of the locations are on an epicardial surface of the tissue. The processor is further configured to assign respective second values to second voxels in the model, a subset of which represent a portion of the tissue between the endocardial surface and the epicardial surface, by interpolating the first values. The processor is further configured to display the model on the monitor.

In some embodiments, the parameter includes a property of the tissue.

In some embodiments, the property includes a local activation time (LAT).

In some embodiments, the processor is further configured to:
identify, based on the first values and the second values, at least one region of decelerating electrical propagation, and
generate an output indicating the region.

In some embodiments, the parameter includes an amount of energy delivered to the tissue.

In some embodiments, the processor is configured to interpolate the first values by iteratively assigning, to each voxel of the second voxels, an average of immediate neighbors of the voxel.

In some embodiments, the processor is configured to assign the average by assigning a weighted average in which the immediate neighbors are weighted by respective weights, which are derived from respective levels of confidence associated with the first values.

In some embodiments, the processor is configured to interpolate the first values by, prior to iteratively assigning the average to each voxel of the second voxels, assigning a respective initial value to each voxel of the second voxels, using any type of nearest neighbor interpolation.

In some embodiments, the processor is configured to display the model so as to indicate those of the second values assigned to the subset.

There is further provided, in accordance with some embodiments of the present invention, a method including assigning, to first voxels in a model of tissue of a chamber of a heart, respective first values of a parameter at respective locations on the tissue, the first voxels representing the locations, respectively. Some of the locations are on an endocardial surface of the tissue, and others of the locations are on an epicardial surface of the tissue. The method further includes assigning respective second values to second voxels in the model, a subset of which represent a portion of the tissue between the endocardial surface and the epicardial surface, by interpolating the first values.

There is further provided, in accordance with some embodiments of the present invention, a computer software product including a tangible non-transitory computer-readable medium in which program instructions are stored. The instructions, when read by a processor, cause the processor to assign, to first voxels in a model of tissue of a chamber of a heart, respective first values of a parameter at respective locations on the tissue, the first voxels representing the locations, respectively. Some of the locations are on an endocardial surface of the tissue, and others of the locations are on an epicardial surface of the tissue. The instructions further cause the processor to assign respective second values to second voxels in the model, a subset of which represent a portion of the tissue between the endocardial surface and the epicardial surface, by interpolating the first values.

The present invention will be more fully understood from the following detailed description of embodiments thereof, taken together with the drawings, in which:

DETAILED DESCRIPTION OF EMBODIMENTS

Overview

In some applications, an electrophysiological map of a portion of a subject's heart is constructed. The electrophysiological map includes a computerized representation of the anatomy of the portion of the heart, along with superimposed electrophysiological data. An example of such a map is an LAT map, which indicates respective LAT values at various anatomical locations using, for example, a sliding color scale.

To construct an LAT map, one or more electrodes at the distal end of a catheter first acquire a "point cloud" of LAT values for various locations on the tissue of the heart. This point cloud is then mapped to a voxelized anatomical model of the tissue, such that the acquired LAT values are assigned, respectively, to a subset of the voxels in the model. Subsequently, using a suitable interpolation technique, the remaining voxels are assigned interpolated LAT values.

Per conventional techniques, two entirely independent LAT maps are constructed for the endocardial and epicardial surfaces of the relevant portion of the heart, respectively. The present inventors have realized, however, that the electrophysiological properties of the endocardial surface of the heart are correlated with those of the epicardial surface, due to the propagation of electrical current through the internal, or "intramural," cardiac tissue. Hence, by virtue of considering each surface in isolation, the aforementioned conventional techniques may provide inaccurate interpolated LAT values.

Hence, embodiments of the present invention provide a volumetric, i.e., three-dimensional, LAT map, which considers both the endocardial and epicardial surfaces, along with the intramural tissue. First, a three-dimensional anatomical model of the cardiac tissue—including the endocardial surface, the epicardial surface, and the intramural tissue—is constructed. Next, respective LAT point clouds are acquired for the endocardial and epicardial surfaces, and the LAT point clouds are mapped to the model. Subsequently, using a suitable interpolation technique, LAT values are estimated for the remaining surface and intramural voxels. For example, an iterative interpolation technique may be used, whereby, during each iteration, each voxel is assigned the average of the values of its immediate neighbors.

Advantageously, the volumetric map that is constructed as described herein is generally accurate for both the endocardial and epicardial surfaces. Moreover, the volumetric map may allow the physician to visualize the electrophysiological properties of the intramural tissue. Furthermore, the volumetric map may facilitate a more accurate identification of regions at which the electrical propagation decelerates.

In addition to local activation times, the techniques described herein may be used to construct volumetric maps for other parameters associated with the tissue. Such parameters include voltage, cycle length, temperature, and an amount of energy delivered to the tissue.

System Description

Figure 1:
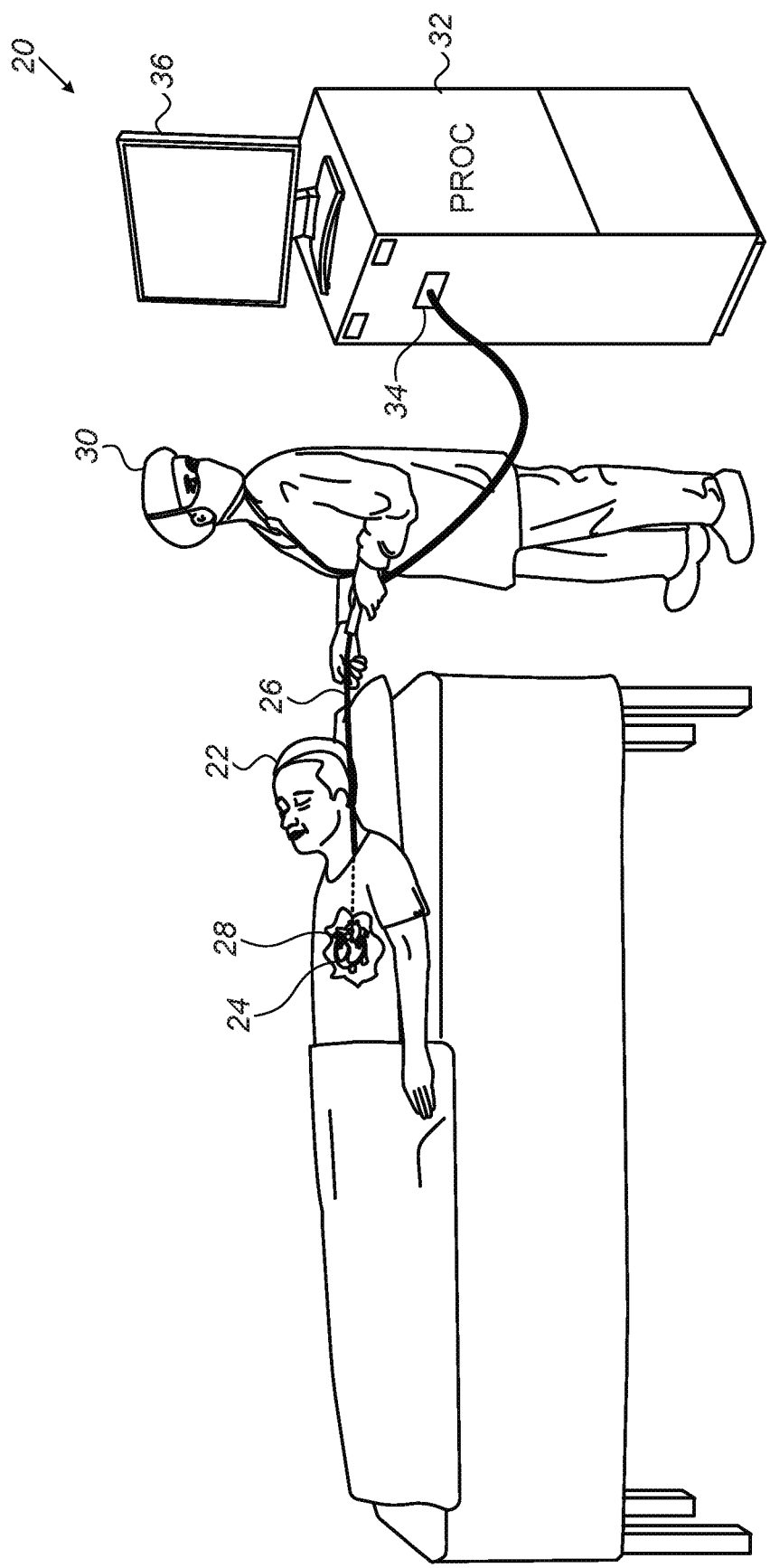
FIG. 1 is a schematic illustration of a system for generating an augmented model of cardiac tissue, in accordance with some embodiments of the present invention.

Reference is initially made to FIG. 1, which is a schematic illustration of a system 20 for generating an augmented model of cardiac tissue, in accordance with some embodiments of the present invention.

In FIG. 1, a physician 30 is shown moving the distal end 28 of a catheter 26 along tissue of a chamber of the heart 24 of a subject 22. In particular, physician 30 moves distal end 28 along both the endocardial surface and epicardial surface of the tissue. In some embodiments, distal end 28 includes one or more treatment electrodes, which may be used to treat (e.g., ablate) one or more areas of tissue.

While the distal end of the catheter is moved along the tissue, a processor 32 belonging to system 20 tracks the distal end, i.e., ascertains the multiple locations on the tissue at which distal end 28 is disposed. (For convenience, each of these locations is referred to hereinbelow simply as the location of the catheter.) As noted above, some of these locations are on the endocardial surface of the tissue, while others are on the epicardial surface of the tissue.

In addition, while the distal end of the catheter is moved along the tissue, electrodes and/or other sensors (e.g., temperature or force sensors) disposed at distal end 28 acquire data related to at least one parameter. These data are received by processor 32 via an electrical interface 34, such as a port or socket. Based on these data, processor 32 ascertains respective values of the parameter at the multiple locations.

Typically, the data acquired by distal end 28 include respective voltage signals at the various locations of the tissue over which distal end 28 is passed. Alternatively or additionally, the data may include respective temperature values at the locations. Alternatively or additionally, the data may include the force with which the catheter presses against the tissue.

In some embodiments, based on the locations of the catheter that are ascertained, processor 32 constructs an anatomical model of the tissue. This anatomical model is then augmented with the values of the aforementioned parameter, as further described below with reference to FIGS. 2-3. In other embodiments, processor 32 augments a preexisting anatomical model with the parameter values.

To facilitate tracking the distal end of the catheter, the distal end of the catheter may comprise one or more electromagnetic sensors, which, in the presence of a generated magnetic field, output signals indicating the respective locations of the sensors. These signals may be received by processor 32 via electrical interface 34. Based on the signals, processor 32 may ascertain the location of the catheter.

Alternatively, the distal end of the catheter may comprise a catheter electrode, and a plurality of electrode patches may be coupled to the body of subject 22. As voltages are applied between the catheter electrode and the electrode patches, the respective magnitudes of the currents between the catheter electrode and the electrode patches may be measured. Based on these current magnitudes, the processor may ascertain the location of the catheter.

As yet another alternative, both of the above-described tracking techniques may be used in combination with one another, as described, for example, in U.S. Pat. No. 8,456,182, whose disclosure is incorporated herein by reference. Alternatively or additionally, any other suitable tracking technique may be used, e.g., as described in U.S. Pat. No. 8,456,182.

Typically, system 20 further comprises a monitor 36. As the physician operates catheter 26, processor 32 may superimpose, on monitor 36, an icon representing the distal end of the catheter over an image of the subject's heart, such that the physician may visually track the catheter. Alternatively or additionally, the processor may display an augmented model of the tissue, which may be constructed as described in detail hereinbelow with reference to FIGS. 2-3, on monitor 36.

In general, processor 32 may be embodied as a single processor, or as a cooperatively networked or clustered set of processors. In some embodiments, the functionality of processor 32, as described herein, is implemented solely in hardware, e.g., using one or more Application-Specific Integrated Circuits (ASICs) or Field-Programmable Gate Arrays (FPGAs). In other embodiments, the functionality of processor 32 is implemented at least partly in software. For example, in some embodiments, processor 32 is a programmed digital computing device comprising a central processing unit (CPU) and/or a graphics processing unit (GPU), random access memory (RAM), non-volatile secondary storage, such as a hard drive or CD ROM drive, network interfaces, and/or peripheral devices. Program code, including software programs, and/or data are loaded into the RAM for execution and processing by the CPU and/or GPU, and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Augmenting the Model

Figure 2:
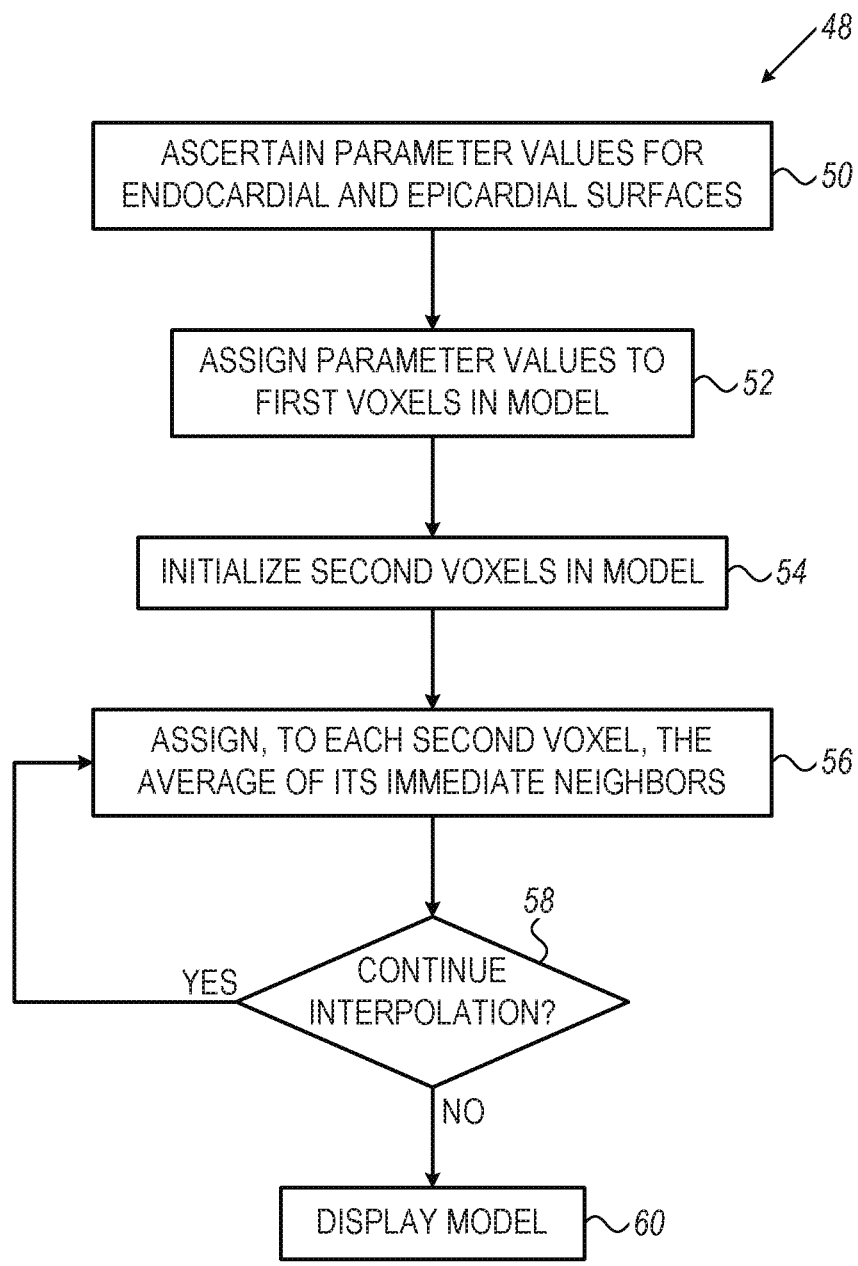
FIG. 2 is a flow diagram for a technique for augmenting a model of cardiac tissue, in accordance with some embodiments of the present invention.
Figure 3:
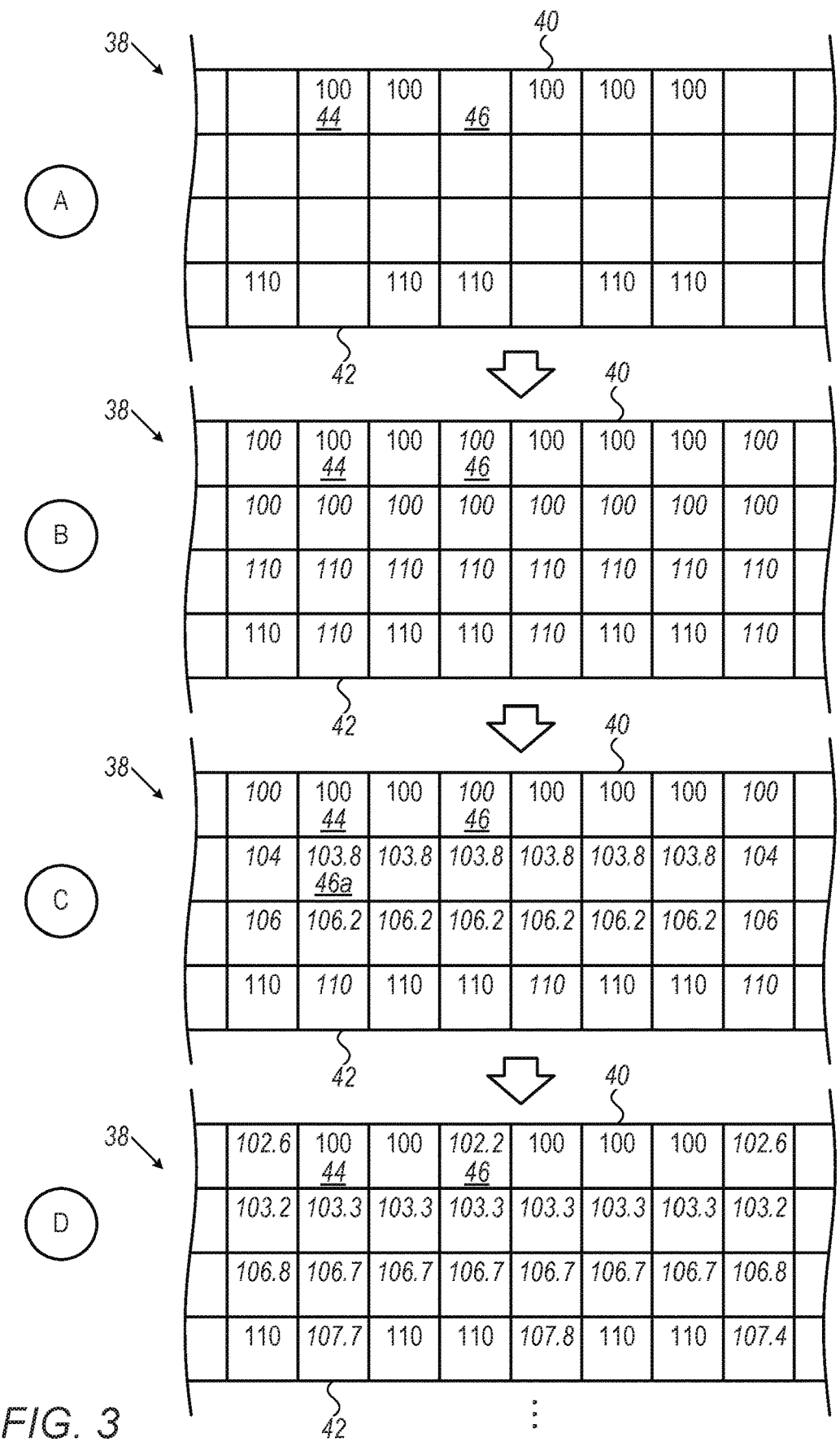
FIG. 3 illustrates aspects of a technique for augmenting a model of cardiac tissue, in accordance with some embodiments of the present invention.

Reference is now made to FIG. 2, which is a schematic illustration of a flow diagram for a technique 48 for augmenting a model of cardiac tissue, in accordance with some embodiments of the present invention. Reference is further made to FIG. 3, which illustrates aspects of technique 48. (It is noted that the quantities shown in FIG. 3 are purely hypothetical, for the sake of illustration.)

As described above with reference to FIG. 1, at an ascertaining step 50, processor 32 ascertains the respective values of a particular parameter at multiple locations on the endocardial and epicardial surfaces of a chamber of heart 24. For example, the processor may ascertain respective values of a property of the tissue, such as the voltage, LAT, cycle-length, or temperature of the tissue. (LAT and cycle-length values may be derived from the voltage signals acquired from the tissue.) Alternatively or additionally, the processor may ascertain respective values of an amount of energy, such as radiofrequency (RF) energy, delivered to the tissue by the treatment electrodes. The amount of energy may be calculated based on factors such as the amount of energy delivered to the treatment electrodes, the temperature of the tissue, and the pressure with which the catheter presses against the tissue.

Subsequently, the processor associates the ascertained values with a three-dimensional model 38 of the tissue. Model 38 includes a plurality of voxels, each voxel representing a different respective portion of the tissue. In particular, those voxels that define a first surface 40 of the model—referred to herein as "epicardial voxels"—represent the epicardial surface of the tissue, those voxels that define a second surface 42—referred to herein as "endocardial voxels"—represent the endocardial surface, and those voxels lying between first surface 40 and second surface 42—referred to herein as "intramural voxels"—represent the intramural tissue. Those voxels representing the respective portions of tissue at which the ascertained parameter values were exhibited are referred to herein as first voxels 44.

More specifically, at a first assigning step 52, the values of the parameter that were ascertained at ascertaining step 50 are assigned to first voxels 44, respectively, as shown in section A of FIG. 3. In other words, each first voxel 44 is assigned the value that was exhibited at the portion of tissue represented by the voxel. Next, as shown in sections B-D of FIG. 3, the processor values (i.e., assigns respective values to) the remaining voxels, referred to herein as second voxels 46, by interpolating the values assigned to first voxels 44. (For clarity, FIG. 3 italicizes the values assigned to second voxels 46.)

Typically, to value the second voxels, the processor first initializes the second voxels at an initializing step 54, i.e., the processor assigns a respective initial value to each second voxel 46. To perform this initialization, the processor may use any suitable type of nearest neighbor interpolation. For example, as shown in section B of FIG. 3, the processor may use a standard nearest neighbor interpolation technique, in that each second voxel may be assigned the value of the first voxel nearest to it. Alternatively, for example, a weighted nearest neighbor interpolation technique may be used for this initialization.

Typically, following the initialization, the processor iteratively assigns, to each second voxel, the average of the respective values of the immediate neighbors of the second voxel. (For embodiments in which the above-described initialization is not performed, the average is performed only over those immediate neighbors to which values were already assigned.) This iterative averaging may be referred to as "Laplace interpolation."

In some embodiments, the number of iterations is predefined. In other embodiments, the processor performs the iterative averaging until one or more predefined stopping criteria are satisfied. For example, the iterative averaging may be performed until the maximum difference between any neighboring pair of voxels is less than a predefined threshold.

Thus, for example, as shown in FIG. 2, the iterative averaging may comprise a second assigning step 56 and a checking step 58. At second assigning step 56, the processor assigns, to each second voxel, the average of its immediate neighbors. At checking step 58, the processor checks whether the predefined number of iterations have been performed, or whether the stopping criteria have been satisfied. If yes, the iterative averaging ends. Otherwise, the processor returns to second assigning step 56.

In some embodiments, one voxel is considered to be an immediate neighbor of (or "adjacent to") another voxel if the two voxels share at least one vertex. Thus, a voxel may have up to 26 immediate neighbors. (Due to the two-dimensional representation of the voxels, FIG. 3 shows a maximum of eight, rather than 26, immediate neighbors.) In other embodiments, two voxels are considered to be immediate neighbors of one another only if the two voxels share at least one face; thus, a voxel may have a maximum of only six immediate neighbors. Alternatively, other criteria may be used for determining the immediate neighbors of a voxel.

By way of illustration, sections C and D of FIG. 3 show two iterations of the above-described averaging, assuming that a pair of voxels sharing at least one common vertex are considered to be immediate neighbors of one another. (It is noted that FIG. 3 does not consider any voxels that are not fully shown in the figure; thus, for example, a corner voxel is valued by averaging only three immediate neighbors.)

In some embodiments, in valuing each second voxel, the immediate neighbors of the second voxel are equally weighted, as assumed in FIG. 3. In other embodiments, the averaged values are weighted by respective weights, which are derived from respective levels of confidence associated with the values assigned to first voxels 44. These levels of confidence are generally a function of the quality with which the relevant data are received from the distal end of the catheter.

For example, supposing that the levels of confidence were greater for the epicardial surface (represented by first surface 40) than for the endocardial surface, the processor might give a greater weight to each epicardial first voxel, along with each "child" second voxel initialized to a value of an epicardial first voxel. Thus, for example, assuming a weight of 1.2 for each epicardial first voxel and the children thereof, and a weight of only 1 for each endocardial first voxel and the children thereof, the particular second voxel 46a shown in section C would be assigned a value of 103.3 (=(1.2*500+330)/(1.2*5+3)), rather than 103.8.

Alternatively or additionally to Laplace interpolation, other interpolation techniques may be used to value second voxels 46. Such techniques include, for example, kriging, inverse distance weighting, spline interpolation, natural neighbor interpolation, and—as already described above—nearest neighbor interpolation. In general, the interpolation techniques are selected responsively to the properties of the interpolated parameter. For example, for local activation times, which vary linearly across the tissue, a linear interpolation technique, such as Laplace interpolation, may be used. For delivered energy, on the other hand, a non-linear, thermodynamics-based interpolation technique may be used. For example, the processor may assume that the amount of delivered energy decays exponentially from the site at which the treatment electrodes contact the tissue.

In some embodiments, second voxels 46 are valued using multiple parallel execution threads running, for example, on a graphics processing unit (GPU). Thus, for example, during each iteration of a Laplace interpolation, all of the second voxels may be processed in parallel.

In some cases, voxels corresponding to scar tissue are not valued, and do not contribute to the valuing of other voxels. Scar tissue may be identified manually by a physician or automatically by processor 32, based on the voltage signals acquired from the tissue.

Typically, subsequently to valuing the second voxels, the processor displays model 38 on monitor 36 (FIG. 1) at a displaying step 60, so as to indicate the values of the parameter. For example, the processor may color the voxels of the model in accordance with a color scale corresponding to the range of values attained by the parameter. As noted above in the Overview, in displaying the model the processor typically indicates the values assigned to the intramural voxels. Thus, advantageously, the physician may obtain a better understanding of the electrical properties of the tissue, relative to if only the endocardial and epicardial surfaces were to be shown.

In some embodiments, based on LAT values assigned to model 38, the processor identifies any regions of decelerating electrical propagation. Advantageously, the three-dimensional nature of model 38 facilitates identifying these regions with greater accuracy.

For example, at each voxel having the coordinates (x0, y0, z0), the processor may compute a normalized velocity of electrical propagation as $V_{(x0,y0,z0)} = ((L_{(x0+1,y0,z0)} - L_{(x0-1,y0,z0)})^{-1}, (L_{(x0,y0+1,z0)} - L_{(x0,y0-1,z0)})^{-1}, (L_{(x0,y0,z0+1)} - L_{(x0,y0,z0-1)})^{-1})$, where $L_{(x,y,z)}$ indicates the LAT at the voxel having the coordinates (x,y,z), (x0±1,y0,z0) are the immediate neighbors of the voxel along the x-axis, (x0,y0±1,z0) are the immediate neighbors of the voxel along the y-axis, and (x0,y0,z0±1) are the immediate neighbors of the voxel along the z-axis. The processor may then compute the derivative of the velocity as $dV = (V_{(x0+1,y0,z0)} - V_{(x0-1,y0,z0)}, V_{(x0,y0+1,z0)} - V_{(x0,y0-1,z0)}, V_{(x0,y0,z0+1)} - V_{(x0,y0,z0-1)})$. Subsequently, the processor may compute the dot product V·dV. If this dot product is negative, the voxel is assumed to represent part of a region of decelerating electrical propagation.

In response to identifying at least one region of decelerating electrical propagation, the processor may generate an output indicating the region. For example, in displaying the model, the processor may color or otherwise annotate the voxels that represent the region.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    a monitor; and
    a processor, configured to:
        assign, to first locations in a model of tissue of a chamber of a heart, respective first values of a parameter, some of the first locations being on an endocardial surface of the tissue, and others of the first locations being on an epicardial surface of the tissue,
        assign respective second values to second locations in the model, a subset of which represent a portion of the tissue between the endocardial surface and the epicardial surface, by interpolating values based on values assigned to respective neighbors of the second locations, and
        display the model on the monitor.

2. The system according to claim 1, wherein the parameter includes a property of the tissue.

3. The system according to claim 2, wherein the property includes a local activation time (LAT).

4. The system according to claim 3, wherein the processor is further configured to:
    identify, based on the first values and the second values, at least one region of decelerating electrical propagation, and
    generate an output indicating the region.

5. The system according to claim 1, wherein the parameter includes an amount of energy delivered to the tissue.

6. The system according to claim 1, wherein the processor is configured to interpolate values based on values assigned to respective neighbors of the second locations by iteratively assigning, to each location of the second locations, an average of values assigned to immediate neighbors of the location.

7. The system according to claim 6, wherein the processor is configured to assign the average by assigning a weighted average in which the immediate neighbors are weighted by respective weights, which are derived from respective levels of confidence associated with the first values.

8. The system according to claim 6, wherein the processor is configured to interpolate values based on values assigned to respective neighbors of the second locations by, prior to iteratively assigning the average to each location of the second locations, assigning a respective initial value to each location of the second locations, using any type of nearest neighbor interpolation.

9. The system according to claim 1, wherein the processor is configured to display the model so as to indicate those of the second values assigned to the subset.

10. A method, comprising:
assigning, to first locations in a model of tissue of a chamber of a heart, respective first values of a parameter at respective locations on the tissue, some of the first locations being on an endocardial surface of the tissue, and others of the first locations being on an epicardial surface of the tissue; and
assigning respective second values to second locations in the model, a subset of which represent a portion of the tissue between the endocardial surface and the epicardial surface, by interpolating values based on values assigned to respective neighbors of the second locations.

11. The method according to claim 10, wherein the parameter includes a property of the tissue.

12. The method according to claim 11, wherein the property includes a local activation time (LAT).

13. The method according to claim 12, further comprising:
based on the first values and the second values, identifying at least one region of decelerating electrical propagation; and
generating an output indicating the region.

14. The method according to claim 10, wherein the parameter includes an amount of energy delivered to the tissue.

15. The method according to claim 10, wherein interpolating values based on values assigned to respective neighbors of the second locations iteratively assigning, to each voxel of the second voxels, an average of immediate neighbors of the voxel.

16. The method according to claim 15, wherein assigning the average comprises assigning a weighted average in which the immediate neighbors are weighted by respective weights, which are derived from respective levels of confidence associated with the first values.

17. The method according to claim 15, wherein interpolating values based on values assigned to respective neighbors of the second locations further comprises, prior to iteratively assigning the average to each location of the second locations, assigning a respective initial value to each location of the second locations, using any type of nearest neighbor interpolation.

18. The method according to claim 10, further comprising displaying the model so as to indicate those of the second values assigned to the subset.

19. A computer software product comprising a tangible non-transitory computer-readable medium in which program instructions are stored, which instructions, when read by a processor, cause the processor to:
assign, to first locations in a model of tissue of a chamber of a heart, respective first values of a parameter at respective locations on the tissue, some of the first locations being on an endocardial surface of the tissue, and others of the first locations being on an epicardial surface of the tissue, and
assign respective second values to second locations in the model, a subset of which represent a portion of the tissue between the endocardial surface and the epicardial surface, by interpolating values based on values assigned to respective neighbors of the second locations.

20. The computer software product according to claim 19, wherein the parameter includes a local activation time (LAT) of the tissue.

* * * * *